United States Patent [19]
Morgan et al.

[11] Patent Number: 5,674,274
[45] Date of Patent: Oct. 7, 1997

[54] IMPLANTABLE ADJUSTABLE SINGLE-PASS A-V LEAD FOR USE WITH AN IMPLANTABLE STIMULATION DEVICE

[75] Inventors: Kevin L. Morgan; Gene A. Bornzin, both of Simi Valley, Calif.

[73] Assignee: Pacesetter, Inc., Sylmar, Calif.

[21] Appl. No.: 572,590

[22] Filed: Dec. 14, 1995

[51] Int. Cl.$^6$ ...................................................... A61N 1/05
[52] U.S. Cl. .......................................... 607/123; 607/122
[58] Field of Search ................................... 607/122, 123, 607/126

[56] References Cited

U.S. PATENT DOCUMENTS

| | | |
|---|---|---|
| 3,865,118 | 2/1975 | Bures . |
| 4,057,067 | 11/1977 | Lajos . |
| 4,289,144 | 9/1981 | Gilman . |
| 4,393,883 | 7/1983 | Smyth et al. . |
| 4,458,677 | 7/1984 | McCorkle, Jr. . |
| 4,479,500 | 10/1984 | Smits . |
| 4,567,901 | 2/1986 | Harris ..................................... 607/123 |
| 4,602,645 | 7/1986 | Barrington et al. . |
| 4,643,201 | 2/1987 | Stokes . |
| 4,664,120 | 5/1987 | Hess . |
| 5,487,385 | 1/1996 | Avitall . |

FOREIGN PATENT DOCUMENTS 0024913  3/1981  European Pat. Off. .

*Primary Examiner*—William E. Kamm
*Assistant Examiner*—Carl H. Layno

[57] ABSTRACT

An adjustable single-pass A-V lead for cardiac pacing comprises a ventricular lead body with a ventricular electrode at its distal tip, and an atrial sheath slidably mounted over the ventricular lead body. An atrial electrode is located on a portion of the atrial sheath that is adapted to form an outwardly-extending atrial bow. A distal portion of the sheath is configured to resist sliding over the ventricular lead body so that the atrial bow is formed when a tubular, proximal portion of the sheath is advanced distally relative to the ventricular lead body. The longitudinal distance between the atrial and ventricular electrodes can be adjusted during implantation by withdrawing the sheath proximally relative to the ventricular lead body. The radial distance between the atrial electrode and the ventricular lead body can then be adjusted by advancing the proximal end of the sheath distally to form the atrial bow, and by manipulating the proximal end of the sheath to control the outward extension of the atrial bow. In an alternative embodiment, the non-tubular portion of the sheath is preformed in a curved configuration, so that the atrial bow forms automatically when a tensional force is released.

33 Claims, 4 Drawing Sheets

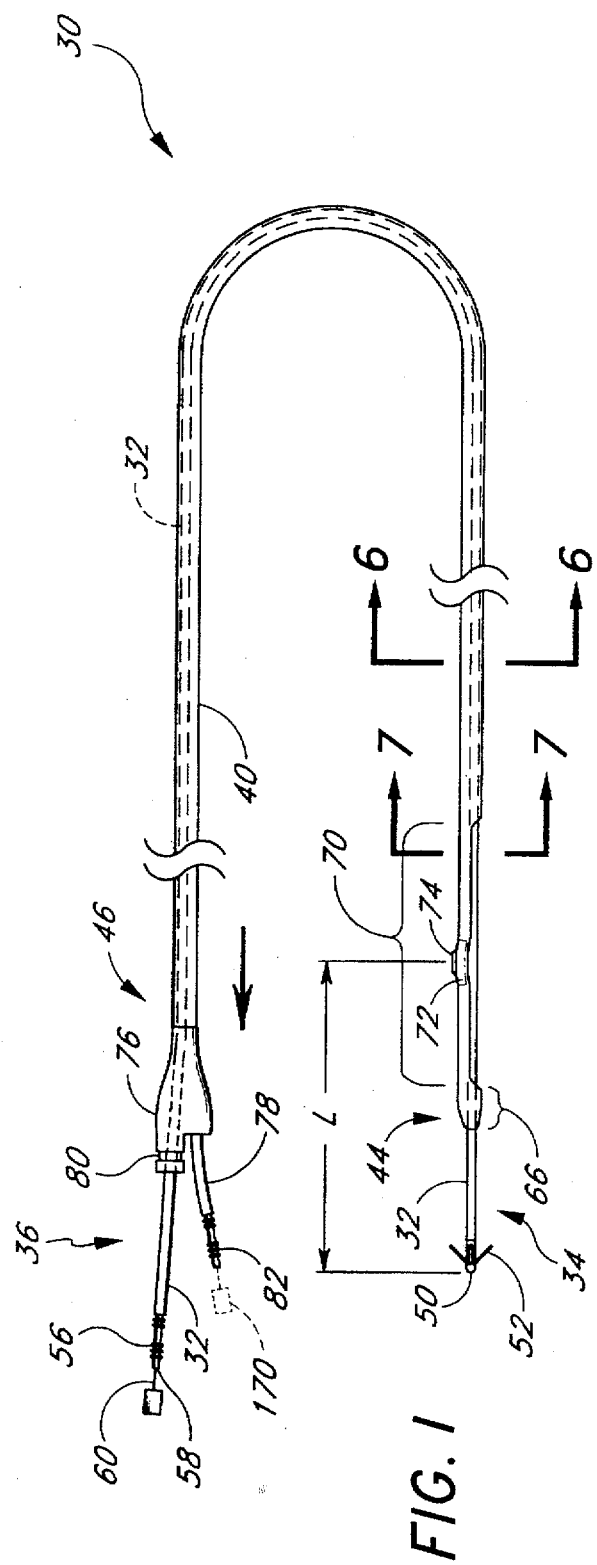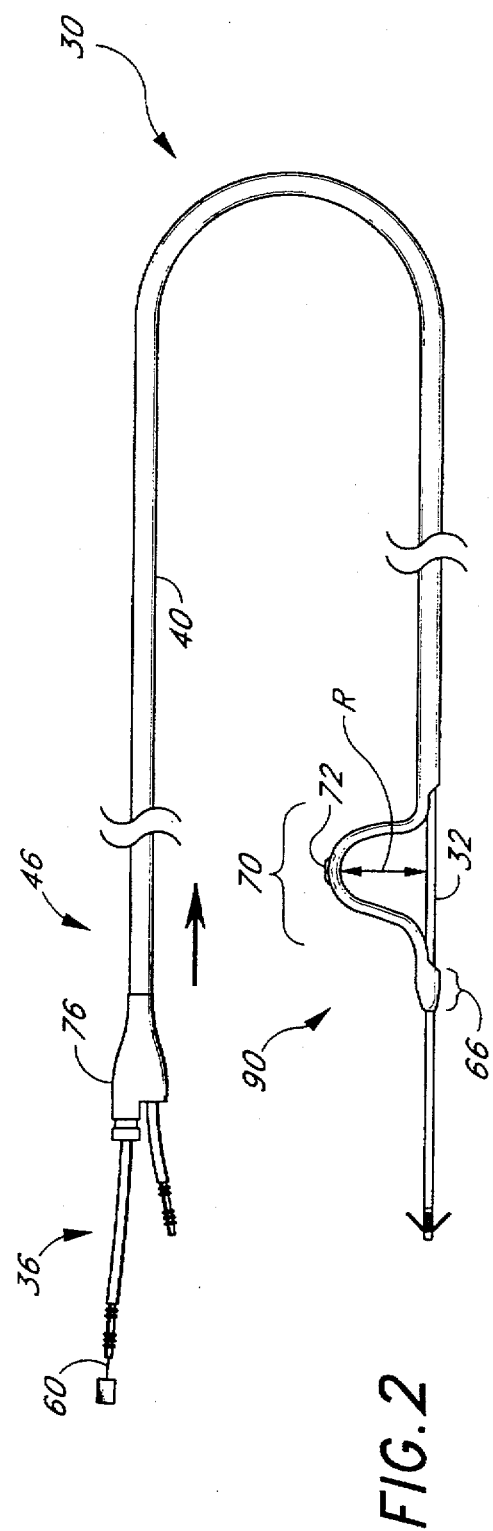

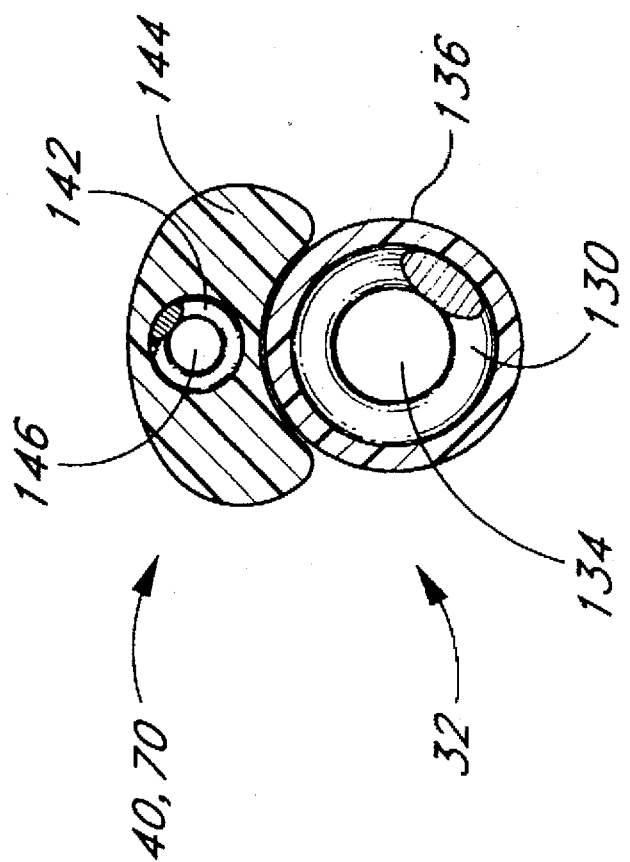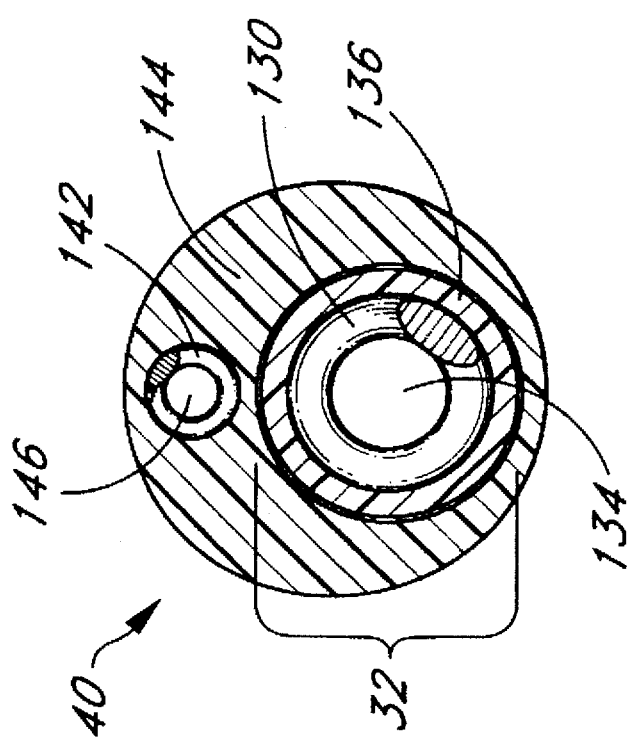

IMPLANTABLE ADJUSTABLE SINGLE-PASS A-V LEAD FOR USE WITH AN IMPLANTABLE STIMULATION DEVICE

FIELD OF THE INVENTION

The present invention relates to electrical leads for implantable cardiac stimulation devices, including bradycardia and antitachycardia pacemakers, defibrillators, cardioverters and combinations thereof. In particular, this invention relates to an implantable single-pass atrial-ventricular (A-V) leads that can be adjusted to accommodate varying sizes of the heart.

BACKGROUND OF THE INVENTION

Cardiac pacing involves the electrical stimulation of the heart in order to control the timing of the contractions of the heart. Electrical stimuli in the form of pulses are generated by a battery-powered pacemaker and applied to the tissue of the heart by one or more electrodes that are connected to the pacemaker via flexible, insulated conductors. The insulated conductors and associated electrodes form what is referred to as the "lead."

For endocardial leads that stimulate the inner walls or "endocardium" of the heart, implantation is typically performed by inserting the distal end of the lead into the patient's cephalic vein (one of the main veins from the upper arm), and forwarding the distal end through the subclavian vein and superior vena cava into the right side of the heart. Once the lead is properly positioned (using fluoroscopy to view the distal end of the lead), the proximal end of the lead is connected to the pacemaker and the pacemaker is implanted beneath the skin.

For various disorders it is desirable to pace the heart by applying separate electrical stimuli to the atrium and the ventricle of the right side of the heart. This form of pacing, commonly known as dual-chamber pacing, generally requires the placement of an atrial electrode in the right atrium and a ventricular electrode in the right ventricle. In addition to applying electrical stimuli to the tissue of the respective chambers, one or both of these electrodes may be used to sense intrinsic electrical activity, and to thereby detect timing abnormalities. For example, the pacemaker may sense the naturally-occurring electrical activity in the right atrium and use this information to generate appropriate electrical stimuli to apply to the right ventricle.

One problem with dual-chamber pacing has been the need to separately position and maintain the atrial and ventricular electrodes in contact with the electrically-sensitive tissue of the respective chambers. The use of separate atrial and ventricular leads permits the independent manipulation and positioning of the atrial and ventricular electrodes. However, the need to pass two separate leads complicates transvenous implantation. To solve this problem, various styles of leads have been designed which include both the atrial and ventricular electrodes on a single lead body, eliminating the need to pass two separate leads. These leads are generally referred to as single-pass atrial-ventricular (A-V) leads.

Because the internal anatomy of the heart varies among individuals, single-pass A-V leads generally must be designed to fit a particular heart size, or else must provide a means for adjusting the relative positions of the atrial and ventricular electrodes. Various lead designs have been proposed that permit adjustment of the relative positions of the electrodes. However, these leads generally do not permit electrode adjustment in multiple dimensions, as is desirable for proper positioning of the electrodes within the heart.

Accordingly, there is a need in the art for a single-pass A-V lead in which the relative positions of the atrial and ventricular electrodes can be adjusted in multiple dimensions once the distal end of the lead has been inserted into the heart. There is also a need for a single-pass A-V lead that can be adjusted during implantation with a minimum number of steps, and that includes a means for holding the electrodes in position following implantation.

SUMMARY OF THE INVENTION

The present invention comprises a single-pass A-V lead that is adjustable to accommodate varying heart sizes. The lead comprises an inner, ventricular lead body having a ventricular electrode at its distal tip. A tubular, atrial sheath is mounted over the ventricular lead body such that at least a portion of the sheath is slidable along the inner, ventricular lead body. An atrial electrode is located on a flexible, non-tubular portion of the sheath. The non-tubular portion is adapted to form an outwardly-extending atrial bow that serves to project the atrial electrode laterally away from the ventricular lead body and against a wall of the right atrium.

The sheath has a distal portion through which the ventricular lead body extends. In the preferred embodiment, the ventricular lead body slidably extends through this distal sheath portion, and the distal sheath portion is configured to resist (but not prevent) the sliding of the ventricular lead body therethrough. The resistance to sliding is sufficient such that, when a slidably-mounted proximal portion of the sheath is advanced distally along the ventricular lead body, the atrial bow forms in the non-tubular portion of the sheath, with the distal sheath portion remaining in fixed position relative to the ventricular lead body.

In the preferred embodiment, the distance between the atrial and ventricular electrodes can be adjusted longitudinally by pulling on the sheath (with a force sufficient to overcome the resistive force provided by the distal sheath portion) so as to slide the sheath proximally along the ventricular lead body. The lateral separation between the atrial electrode and the ventricular lead body can then be adjusted by sliding a proximal portion of the sheath distally along the ventricular lead body to form the atrial bow, and by manipulating the proximal portion to control the laterally outward extension of the bow. These adjustment features of the lead permit the lead to be adjusted to accommodate varying dimensions within the heart. Specifically, the longitudinal distance between the electrodes can be adjusted to accommodate varying distances between the right ventricular apex and the right atrium, and the outward projection of the atrial bow can be adjusted to accommodate varying widths of the right atrium.

To implant the lead, the lead is initially advanced into the heart until the ventricular electrode is in the right ventricular apex. The sheath is then withdrawn proximally along the ventricular lead body (under fluoroscopic observation) to increase the longitudinal separation of the atrial and ventricular electrodes and to position the atrial electrode within the right atrium. The proximal end of the sheath is then advanced distally along the ventricular lead body to form the atrial bow, with the bow being formed such that the atrial electrode is pressed against the wall of the right atrium. The above implantation steps are preferably performed with a guidewire or "stylet" inserted within a lumen of the ventricular lead body to maintain the ventricular lead body in a relatively stiff condition. Once the atrial bow has been formed and the atrial and ventricular electrodes are properly positioned within the heart, the stylet is removed, and the proximal end of the sheath is fixedly attached to the ventricular lead body (using a suture or other conventional attachment means) to maintain the configuration of the atrial bow. The atrial bow thereafter serves to bias the atrial electrode against a wall of the right atrium, and further serves to maintain the electrodes in their respective positions within the heart.

In another embodiment, the distal portion of the sheath is fixedly attached to the ventricular lead body. In this alternative embodiment, the laterally outward extension of the atrial bow can be adjusted, but the longitudinal distance between the electrodes remains fixed.

In yet another embodiment, an atrial lumen extends longitudinally within the sheath and through the non-tubular sheath portion, permitting the insertion of an atrial stylet. The atrial stylet may be inserted during the implantation procedure to hold the non-tubular sheath portion in a substantially straight configuration so that the sheath can be advanced distally along the ventricular lead body (as might be desirable if the sheath is withdrawn too far in the proximal direction). The atrial stylet can further be used to facilitate straightening of the atrial bow when it is desirable to remove a previously-implanted lead from the heart.

In yet another embodiment, the flexible, non-tubular sheath portion is preformed to assume a curved configuration so as to facilitate formation of the atrial bow. The preformed, non-tubular sheath portion may be held in a substantially straight configuration during implantation by applying a tension force to the non-tubular sheath portion, or, for embodiments that include an atrial lumen, by inserting an atrial stylet.

BRIEF DESCRIPTION OF THE DRAWINGS

FIG. 1 is a plan view of a single-pass A-V lead in accordance with the present invention.

FIG. 2 is a plan view of the lead of FIG. 1, showing an outwardly-extending atrial bow formed in a non-tubular sheath portion of the lead.

FIG. 6 is a cross-sectional view taken on the line 6—6 of FIG. 1.

FIG. 7 is a cross-sectional view taken on the line 7—7 of FIG. 1.

DETAILED DESCRIPTION OF THE PREFERRED EMBODIMENTS

Figure 5:
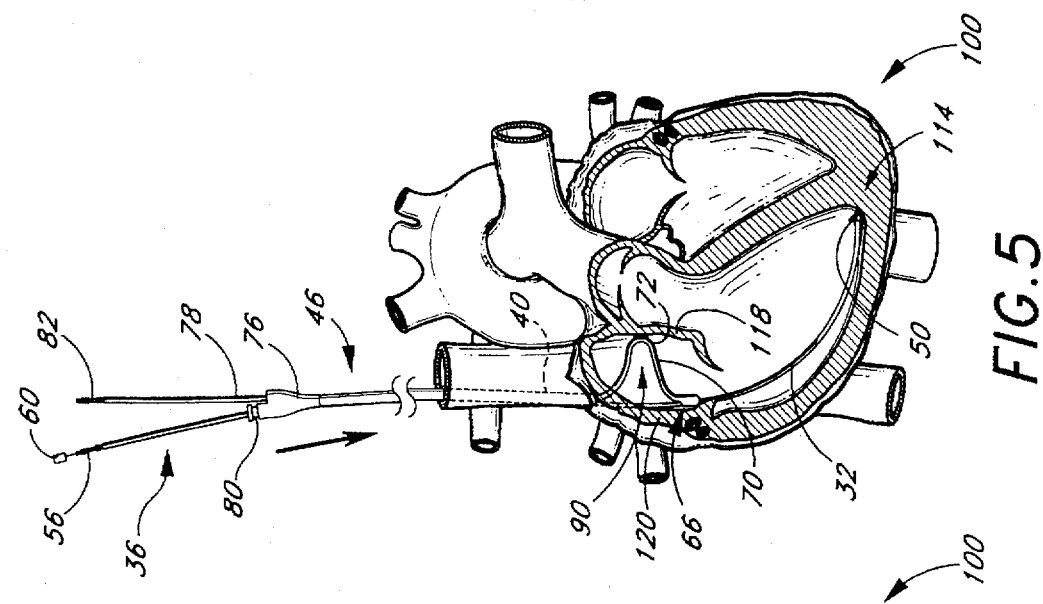
FIG. 5 is a perspective view in partial cross-section, illustrating the configuration of the lead of FIG. 4 following formation of the atrial bow.

FIGS. 1–8 illustrate a single-pass A-V lead 30 in accordance with the present invention. The lead 30 shown is a unipolar lead, having a single atrial electrode and a single ventricular electrode. However, as will be recognized by those skilled in the art, aspects of the present invention are also applicable to bipolar and semi-bipolar single-pass A-V leads that have three or more electrodes. Additionally, while the present invention will be described for use with a cardiac pacemaker (e.g., a bradycardia pacemaker), the present invention could be adapted for use with antitachycardia pacemakers, defibrillators, cardioverters and combinations thereof without departing from the spirit of the invention.

As shown in FIG. 1, the lead 30 comprises an elongated, insulated, ventricular lead body 32 having a distal end 34 and a proximal end 36. The ventricular lead body 32 is slidably mounted within a flexible, tubular sheath 40 that has a distal end 44 and a proximal end 46. The ventricular lead body 32 is shown in dashed lines where it passes through tubular portions of the sheath 40. The ventricular lead body 32 has a greater longitudinal length than the tubular sheath 40 so that the sheath 40 can be slidably adjusted along the ventricular lead body 32.

The ventricular lead body 32 has a ventricular electrode 50 located at its distal tip. The ventricular electrode 50 is suitable for placement within the right ventricular apex of the heart. The ventricular electrode 50 shown is a passive fixation type electrode, having flexible tines 52 to accommodate the growth of fibrous tissue around the electrode 50. However, as will be recognized by those skilled in the art, an active fixation type electrode that uses a barb or screw to hold the electrode 50 in position could alternatively be used.

The ventricular lead body 32 has a pin connector 56 at its proximal end 36 that is adapted for connection to a pacemaker (pacemaker not shown). The pin connector 56 has a port 58 that is adapted for the insertion of a guidewire or "stylet" 60. A hollow channel or "lumen" 134 (FIGS. 6 and 7) extends axially from the port 58 through the ventricular lead body 32 and into the distal end 34 of the ventricular lead body 32, permitting the stylet 60 to be inserted up to the ventricular electrode 50.

Figure 8:
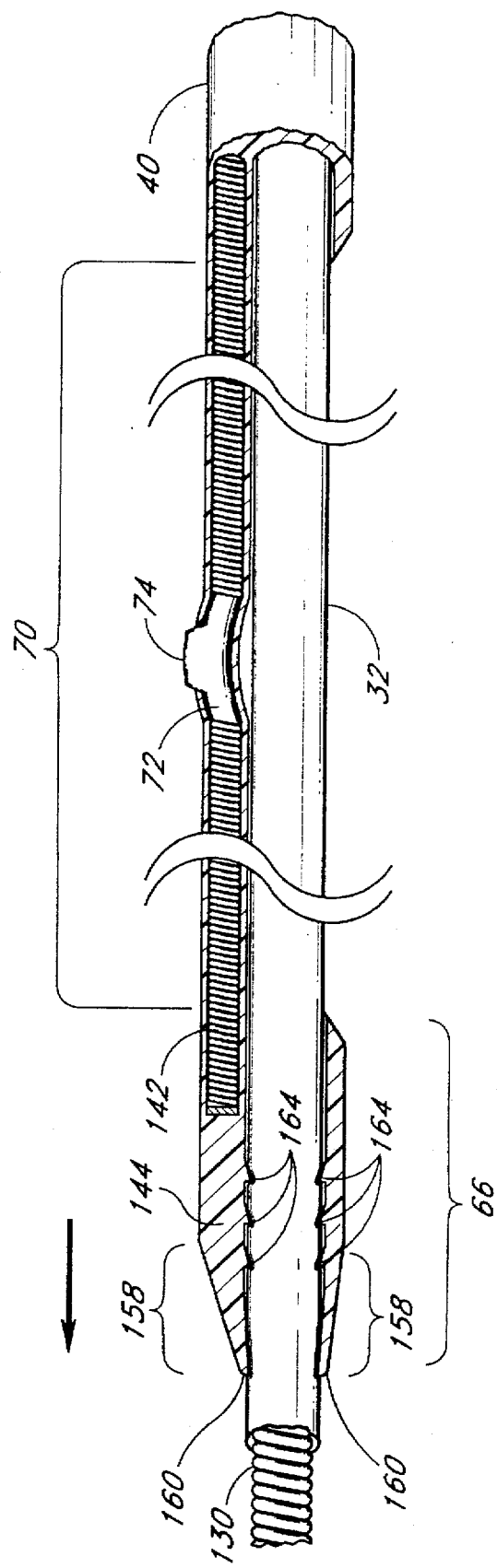
FIG. 8 is a plan view of a portion of the lead of FIG. 1, with component parts thereof cut away to reveal the construction of the lead.

The sheath 40 has a distal portion 66 (hereinafter "distal sheath portion 66") through which the ventricular lead body 32 extends. In the preferred embodiment, the ventricular lead body 32 slidably extends through the distal sheath portion 66, the distal sheath portion 66 is configured to resist the sliding of the ventricular lead body 32 therethrough. Such a resistance can be provided, for example, by configuring the distal sheath portion 66 to fit tightly around the ventricular lead body 32 such that a resistance to sliding is provided byway of friction between the inner surface of the distal sheath portion 66 and the outer surface of the ventricular lead body 32. Other conventional means for producing a resistance to sliding can additionally or alternatively be employed, including ridges or interlocking teeth that resist sliding in one or both directions. A preferred configuration of the distal sheath portion 66 is shown in FIG. 8 and discussed below. In an alternative embodiment, the distal sheath portion 66 is fixedly attached to the ventricular lead body 32.

Extending proximally from the distal sheath portion 66, the sheath 40 has a pliant, non-tubular portion 70 that is adapted to form an outwardly-extending atrial bow 90 (FIGS. 2 and 5) when a compressive force is applied to the non-tubular portion 70. An atrial electrode 72 is formed in-line with the non-tubular portion 70 at a central region of the non-tubular portion 70. The atrial electrode 72 preferably has a fixed, curved configuration as shown. A protrusion 74 of the electrode 72 extends outwardly away from the non-tubular portion 70 in a radial direction relative to the ventricular lead body 32.

The proximal end 46 of the sheath 40 is connected to a bifurcated-transition boot 76. The boot 76 is preferably formed from silicone rubber. The boot 76 has a hollow channel through which the ventricular lead body 32 slidably extends (as shown in dashed lines in FIG. 1). The boot 76 rigidly connects the sheath 40 to a connector branch 78. The connector branch 78 has a pin connector 82 at its proximal end that is adapted for connection to a pacemaker. The connector branch 78 and sheath 40 form an atrial lead body that can be manipulated in position relative to the ventricular lead body 32.

A suture groove 80 extends circumferentially around a portion of the boot 76, permitting the boot 76 to be suture-tied to the ventricular lead body. The boot 76 and suture groove 80 are formed such that the inner walls of the boot 76 constrict the ventricular lead body 32 when a suture is tied within the groove 80. The suture groove 80 permits a physician to fix the slidably-mounted proximal portion of the sheath 40 (i.e., the portion of the sheath 40 proximal to the non-tubular portion 70) in position relative to the ventricular lead body 32 following implantation, as is necessary for maintaining the configuration of the atrial bow 90 (FIGS. 2 and 5). If desired, additional suture grooves (not shown) can be provided along the boot 76 to distribute the constricting force over a larger segment of the ventricular lead body 32. As will be recognized by those skilled in the art, any other suitable attachment means can be used to fix the slidably-mounted proximal portion of the sheath 40 to the ventricular lead body 32. For example, a conventional suture sleeve (not shown) can be used, which may be provided circumferentially around a proximal segment of the sheath 40 to permit constriction of ventricular lead body 32 when a suture is tied around the suture sleeve.

Still referring to FIG. 1, the longitudinal distance L between the ventricular electrode 50 and the atrial electrode 72 can be manually adjusted by sliding the sheath 40 distally along the ventricular lead body 32. Adjustment is preferably accomplished by holding the proximal end 36 of the ventricular lead body 32 in a fixed position while pulling proximally on the boot 76 (in the direction of the arrow in FIG. 1) with a force that is sufficient to overcome the resistive force provided by the distal sheath portion 66. The stylet 60 is preferably fully inserted during such longitudinal adjustment to maintain the ventricular lead body 32 in a relatively stiff condition. Adjustment of the lead 30 in this manner permits accommodation for varying distances between the right ventricular apex and the right atrium. For embodiments of the lead 30 having a distal sheath portion 66 that is fixedly attached to the ventricular lead body 32, adjustment of the longitudinal distance L cannot be performed.

As shown in FIG. 2, when the proximal end 46 of the sheath 40 is advanced distally (in the direction of the arrow in FIG. 2), the resistive force provided by the distal sheath portion 66 is sufficient to prevent the distal sheath portion 66 from sliding, causing an outwardly-extending atrial bow 90 to form in the non-tubular portion 70 (in response to the compressive force applied to the non-tubular portion 70). The bow 90 serves to lodge the atrial electrode 72 against the wall of the right atrium when the lead 30 is properly positioned within the heart. The curvature of the atrial electrode 72 facilitates the formation of the bow 90 when the proximal end 46 of the sheath 40 is initially advanced distally, and further helps to maintain the atrial electrode 72 at an outermost portion of the bow 90.

Once the bow has been formed, the lateral distance between the atrial electrode 72 and the ventricular lead body 32 (shown in FIG. 2 as the radial distance R) can be manually adjusted by manipulating the proximal end 46 of the sheath 40 relative to the ventricular lead body 32 to control the configuration of the bow 90. The lead 30 can thereby be adjusted to accommodate varying widths of the right atrium. The distance R can be increased (up to a maximum) by advancing the proximal end 46 of the sheath 40 distally to increase the outward extension of the bow 90. The distance R can be decreased by withdrawing the proximal end 46 of the sheath 40 proximally to decrease the outward extension of the bow 90. Adjustment of the distance R can be accomplished by holding the proximal end 36 of the ventricular lead body 32 in a fixed position while moving the boot 76, with the stylet 60 fully inserted to maintain the ventricular lead body 32 in a relatively stiff condition.

Figure 4:
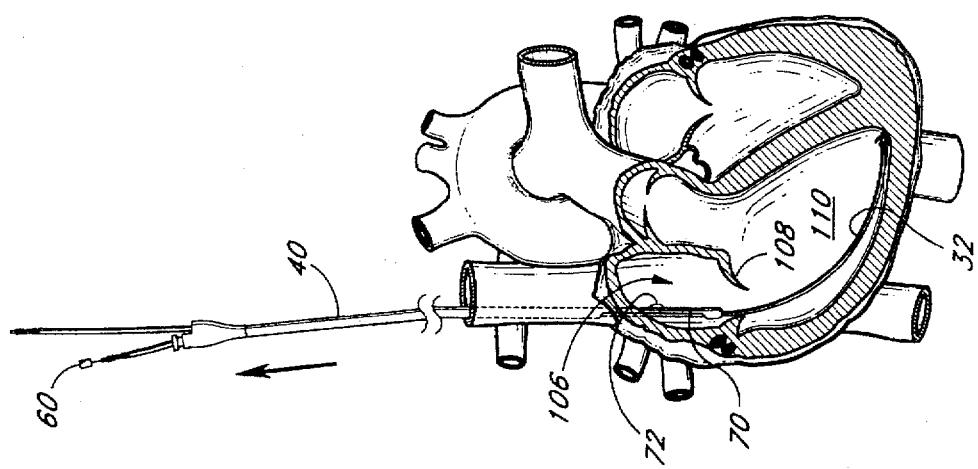
FIG. 4 is a perspective view in partial cross-section, illustrating the lead of FIG. 3 after manipulating the lead to increase the longitudinal distance between the atrial and ventricular electrodes to correspond to the distance between the ventricular apex and the right atrium.
Figure 3:
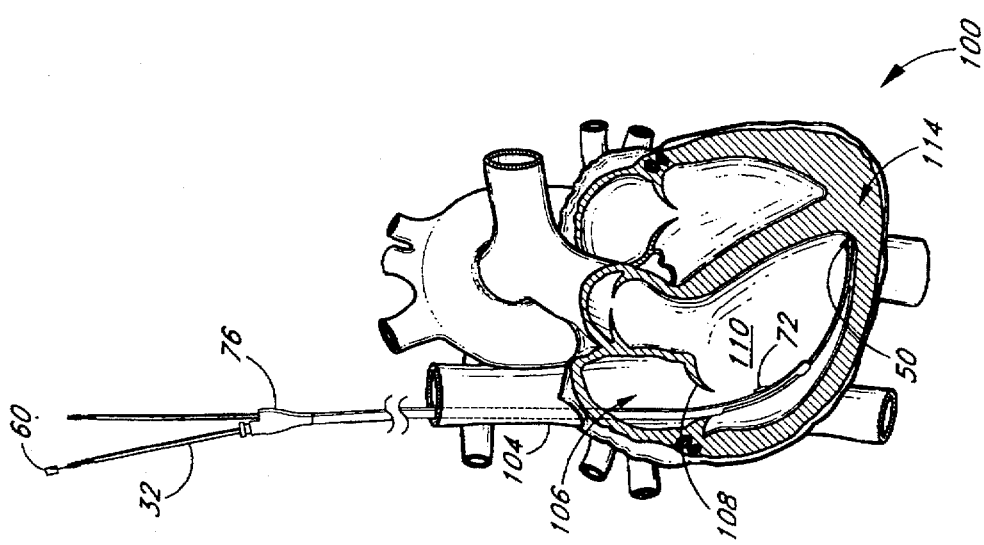
FIG. 3 is a perspective view in partial cross-section, illustrating the position of the lead of FIG. 1 after insertion into a human heart.

FIGS. 3–5 illustrate the steps of the implantation procedure that are performed to adjust the lead 30 for a particular heart 100. Referring to FIG. 3, using transvenous implantation procedures that are well known in the art, the distal end of the lead 30 is initially advanced through the superior vena cava 104, right atrium 106, and tricuspid valve 108 and into the right ventricle 110, with the ventricular electrode 50 placed in the right ventricular apex 114 as shown. The lead 30 is advanced to this position with the stylet 60 fully inserted to maintain the ventricular lead body 32 in a relatively stiff condition. The use of a stylet 60 to facilitate transvenous implantation is well known in the art. The lead 30 is advanced to the position shown with the aid of fluoroscopy, which permits the physician to view the metallic portions of the lead 30 as the lead 30 is passed through the venous system and positioned within the heart 100. As shown in FIG. 3, the lead 30 is configured for a smaller than expected heart size upon insertion, with the atrial electrode 72 falling low in the right atrium 106 or below the tricuspid valve 108.

Referring to FIG. 4, once the lead 30 has been advanced to the position shown in FIG. 3, the sheath 40 is withdrawn proximally (in the direction of the arrow in FIG. 4) relative to the ventricular lead body 32 to position the atrial electrode 72 within the right atrium 106. The atrial electrode 72 is so positioned under continuous fluoroscopic observation, and with the stylet 60 fully inserted. The atrial electrode 72 is preferably positioned somewhat high in the right atrium 106 during this step of the procedure to account for a downward movement of the atrial electrode 72 that results when the atrial bow 90 (FIG. 5) is formed.

It is also desirable during this step of the procedure to position the entire length of the non-tubular portion 70 above the tricuspid valve 108 as shown, so that the atrial bow 90 (FIGS. 2 and 5) will be fully contained within the right atrium 106 once formed. It is thus desirable to provide a means for permitting the physician to view the entire length of the non-tubular portion 70 during the implantation procedure. In the preferred embodiment, a helical coil conductor 142 (FIGS. 6–8) extends through the non-tubular portion 70 and into the distal sheath portion 66 (as shown in FIG. 8), providing such a means for allowing the physician to view the entire length of the non-tubular portion 70. Alternatively, a radio-opaque marker can be provided at or near the distal sheath portion 66.

For embodiments of the lead 30 that have a distal sheath portion 66 that is fixedly attached to the ventricular lead body 32, the step of sliding the sheath 40 proximally along the ventricular lead body 32 is not performed. A particular lead size is thus selected that corresponds to the expected distance between the right ventricular apex and the right atrium.

Referring to FIG. 5, once the sheath 40 has been withdrawn proximally as described above, the proximal end 46 of the sheath 40 is advanced distally (in the direction of the arrow in FIG. 5) along the ventricular lead body 32 to form the atrial bow 90. The stylet 60 remains inserted during this step of the procedure. The proximal end 46 of the sheath 40 may be distally advanced by pushing downward on the boot 76 while holding the proximal end 36 of the ventricular lead body 32 in a fixed position. Alternatively, a downward force may be applied to the boot 76 without holding the ventricular lead body 32, in which case a counteracting force generated by the application of the stiffened ventricular lead body 32 to the ventricular apex 114 permits proximal advancement of the sheath 40 along the ventricular lead body 32. The proximal end 46 of the sheath 40 is advanced until the atrial electrode 72 presses against the wall 118 and the ventricular lead body 32 presses against the atrial free wall 120, as shown in FIG. 5. The biasing forces generated by the outward expansion of the atrial bow 90 serve to hold the atrial electrode 72 and the distal portion of the lead 30 in position following implantation, while maintaining the atrial electrode 72 in good electrical contact with the electrically conductive tissue of the right atrium 106.

Once the electrodes 50, 72 have been properly positioned within the heart 100 as shown in FIG. 5, the stylet 60 is fully withdrawn from the ventricular lead body 32. The proximal end 46 of the sheath 40 is then suture-tied to the ventricular lead body 32 (using the suture groove 80, a suture sleeve, or any other suitable fixation means) to prevent the slidably-mounted proximal portion of the sheath from sliding relative to the ventricular lead body 32 following implantation. To align the pin connectors 56 and 82 with each other for connection to a pacemaker, a bow (not shown) may be formed in either the connector branch 78 or the proximal end 36 of the ventricular lead body 32 if necessary. Following implantation, the resistive force provided by the distal sheath portion 66 prevents the distal sheath portion 66 from sliding. The ends of the sheath 40 are thus held in fixed positions relative to the ventricular lead body 32, and the atrial bow 90 is maintained in the desired configuration.

FIG. 6 illustrates the internal composition of the lead 30 in the region between the non-tubular portion 70 and the boot 76. The ventricular lead body 32 comprises a flexible conductor 130 that conductively connects the pin connector 56 (FIG. 1) to the ventricular electrode 50. The conductor 130 is preferably formed as a helical coil as shown, as is conventional in the art. The inner walls of the helical coil conductor 130 form the lumen 134 through which the stylet 60 is passed. The helical coil conductor 130 is coated with an insulating material 136.

The sheath 40 comprises a second helical coil conductor 142. The helical coil conductor 142 extends through the connector branch 78 (FIG. 1), and conductively connects the pin connector 82 (FIG. 1) to the atrial electrode 72. The conductor 142 is formed within an insulating material 144. The insulating materials 136 and 144 are preferably silicone rubber, but may comprise other flexible, biocompatible materials that are known in the art, including, but not limited to, polyurethane, the material sold under the trademark Teflon® (manufactured by DuPont), and polyethylene.

FIGS. 7 and 8 illustrate the construction of the non-tubular and distal portions 70, 66 of the sheath 40. Referring to FIG. 7, the inward-facing surface of the non-tubular portion 70 of the sheath 40 is configured so as to conform to the outer surface of the ventricular lead body 32. Referring to FIG. 8, the helical coil conductor 142 passes through a hollow portion of the atrial electrode 72 (conductively contacting the atrial electrode 72 as it passes through), and extends distally into the distal sheath portion 66. The helical coil conductor 142 advantageously maintains a generally constant degree of flexibility throughout the entire length of the non-tubular portion 70, as is desirable for controlling the configuration of the atrial bow 90 (FIGS. 2 and 5).

Referring to FIG. 8, a distal-most portion 158 of the sheath 40 is configured to fit tightly around the ventricular lead body 32 so as to provide a resistance against sliding by way of friction. The walls of the insulating layer are 144 tapered in the distal-most portion 158, with the insulating layer 144 reaching its minimum thickness at the distal tip 160. This causes the distal-most portion 158 of the insulating layer 144 to essentially "bunch-up" or expand so as to constrict the ventricular lead body 32 when the sheath 40 is pushed distally (in the direction of the arrow in FIG. 8) relative to the ventricular lead body 32. The tapered configuration of the distal-most portion thereby serves to increase the resistance against sliding when the sheath 40 is advanced distally (in comparison to the resistance against sliding when the sheath 40 is withdrawn proximally), as is desirable to facilitate adjustment of the lead 30. A further increase in the resistance to the distal movement of distal sheath portion 66 is provided by ridges 164 along the inner walls of the distal sheath portion 66.

Referring to FIGS. 6–8, the inner walls of the helical coil conductor 142 form an atrial lumen 146 (FIGS. 6 and 7). The atrial lumen 146 extends through the non-tubular portion 70 (including the atrial electrode 72), and terminates at the distal sheath portion 66 (FIG. 8). In one embodiment of the lead 30, the atrial lumen 146 extends through the connector branch 78 (FIG. 1) and the pin connector 82 (FIG. 1), and is adapted for the insertion of an atrial stylet 170 (shown in dashed lines in FIG. 1). The atrial stylet 170 can be inserted during an implantation procedure to stiffen the non-tubular portion 70 so that the distal sheath portion 66 can be advanced distally along the ventricular lead body 32. Such distal advancement of the distal sheath portion 66 may be desirable, for example, if a physician proximally withdraws the sheath 40 too far during the step of the implantation procedure illustrated by FIG. 4. It is also contemplated that the atrial stylet 170 may be used to straighten the non-tubular portion 70 to facilitate removal of a previously-implanted lead 30 from a patient. In other embodiments of the lead 30, the atrial lumen 146 does not extend through the pin connector 82 (FIG. 1).

Referring to FIG. 2, in a further alternative embodiment the non-tubular portion 70 of the sheath 40 is preformed in a curved configuration using techniques that are well known in the art. The preformed curve or bend is configured such that the atrial bow 90 forms automatically when no tensional force is applied to the non-tubular portion 70. The preformed bend may be formed in either or both of the insulating material 144 (FIGS. 6–8) or the helical coil conductor 142 (FIGS. 6–8). To straighten the preformed bow 90 of the non-tubular portion 70 during implantation, a tension force is applied to the non-tubular portion 70 by pulling proximally on the boot 76 relative to the ventricular lead body 32, using a force that is sufficient to substantially straighten the preformed portion 70 but insufficient to overcome the resistive force provided by the distal sheath portion 66. In embodiments of the lead 30 that are configured for insertion of an atrial stylet 170 (FIG. 1), the non-tubular portion 70 may alternatively be held in a substantially straight configuration for implantation by insertion of the atrial stylet 170. When the force used to hold the preformed non-tubular portion 70 in a straight configuration is removed (by releasing the boot 76 or by removing the atrial stylet 170), the resilience of the preformed portion is sufficient to pull the slidably-mounted tubular portion of the sheath 40 (i.e., the portion of the sheath 40 proximal to the non-tubular portion 70) distally along the ventricular lead body 32. The atrial bow 90 thus forms automatically in a spring-like manner, obviating the need to advance the proximal end 46 of the sheath 40 distally.

While various embodiments of an adjustable single-pass A-V lead have been described, these embodiments have been presented by way of example only, and are not intended to limit the scope of the present invention. Thus, the breadth and scope of the present invention should be defined only in accordance with the following claims and their equivalents.

What is claimed is:

1. An adjustable, single-pass implantable cardiac stimulation lead, comprising:
   a first member having an atrial electrode; and
   a second member having a ventricular electrode, the second member slidably attached to the first member such that at least a first portion of the first member is slidable relative to the second member, at least one of the members having a locking portion that secures the members together to prevent sliding of a second portion of the first member relative to the second member while permitting the sliding of the first portion relative to the second member, whereby the sliding causes a bow to be formed in a bowing portion of the first member;
   wherein the locking portion comprises a friction fitting that resists the sliding of the second portion of the first member relative to the second member.

2. The lead according to claim 1, wherein the second member is slidably mounted within a tubular portion of the first member, and wherein the atrial electrode is on the bowing portion of the first member.

3. The lead according to claim 2, wherein the bowing portion of the first member comprises a resilient member which is preformed such that the resilient member urges the bowing portion to assume a curved configuration.

4. The lead according to claim 1, wherein the locking portion comprises a tubular portion of the first member that is configured to fit tightly around the second member.

5. The lead according to claim 1, wherein the resistance to sliding is provided at least in-part by friction between an inner wall of the second portion and an outer wall of the first member, and wherein at least one of the inner wall and the outer wall is configured such that a resistance to movement of the second portion relative to the first member is greater for distal relative movement than for proximal relative movement.

6. The lead according to claim 5, wherein the inner wall comprises a plurality of ridges which contact the outer wall of the first member to provide at least a portion of the resistance to said distal relative movement.

7. The lead according to claim 1, wherein the atrial electrode is formed in-line with the bowing portion, and wherein the atrial electrode has a fixed, curved configuration to facilitate formation of the bow when a compressive force is applied to the bowing portion.

8. The lead according to claim 1, wherein the first member has a lumen formed therein, the lumen adapted for the insertion of an atrial stylet, the lumen extending into the bowing portion so that the bowing portion is held in a substantially straight configuration when the atrial stylet is inserted within the lumen.

9. The lead according to claim 1, wherein the second member has a lumen that extends axially from a proximal end of the second member substantially to a distal end of the second member, the lumen adapted for the insertion of a stylet.

10. An implantable single-pass A-V lead that is adjustable to accommodate varying heart sizes, comprising:
    an inner, ventricular lead body having a proximal end for connection to an implantable stimulation device and a distal end for placement within the right ventricle;
    a ventricular electrode at the distal tip of the ventricular lead body;
    an atrial lead body having an outer, tubular sheath with at least a first portion of the sheath being slidably mounted over the ventricular lead body, the sheath having a distal end and a proximal end, the sheath further having a flexible, bowing portion which forms an outwardly-extending atrial bow when the first portion of the sheath is advanced in a distal direction relative to the ventricular lead body; and
    an atrial electrode on the flexible, bowing portion of the sheath;
    wherein the sheath has a lumen formed therein, the lumen adapted for the insertion of an atrial stylet, the lumen extending into the bowing portion so that the bowing portion is held in a substantially straight configuration when the atrial stylet is inserted.

11. The implantable single-pass A-V lead, according to claim 10, wherein a distal portion of the sheath is fixedly attached to the ventricular lead body.

12. The implantable single-pass A-V lead, according to claim 10, wherein the atrial electrode is formed in-line with the bowing portion, and wherein the atrial electrode has a fixed, curved configuration to facilitate formation of the atrial bow when a compressive force is applied to the bowing portion.

13. The implantable single-pass A-V lead, according to claim 10, wherein the atrial electrode is positioned on a central region of the flexible bowing portion, and a preformed bend in the bowing portion is configured such that a distance between the atrial electrode and the ventricular lead body increases as the sheath is advanced in the distal direction relative to the ventricular lead body.

14. The implantable single-pass A-V lead, according to claim 7, wherein the bowing portion comprises a resilient, elongate member which is preformed to urge the bowing portion to assume a curved configuration when a tensional force is released from the bowing portion.

15. The implantable single-pass A-V lead, according to claim 10, wherein the ventricular lead body has a lumen that extends axially from the proximal end of the ventricular lead body substantially to the distal end of the ventricular lead body, the lumen adapted for the insertion of a stylet.

16. The implantable single-pass A-V lead, according to claim 10, wherein a distal portion of the sheath is tightly coupled to the ventricular lead body such that a resistance is created to distal movement of the distal portion of the sheath relative to the ventricular lead body.

17. The implantable single-pass A-V lead, according to claim 16, wherein a portion of the ventricular lead body along which the sheath is slidable has a length which exceeds a total length of the sheath, so that a position of the atrial electrode relative to the ventricular electrode is longitudinally adjustable by sliding the sheath proximally relative to the ventricular lead body, and wherein the bowing portion is sufficiently elongated and flexible to allow a curvature of the atrial bow to be increased by sliding the first portion of the sheath distally along the ventricular lead body, an increase is said curvature causing an increase in a lateral displacement of the atrial electrode relative to the ventricular lead body so that the position of the atrial electrode relative to the ventricular lead body is laterally adjustable.

18. The implantable single-pass A-V lead, according to claim 16, wherein the distal portion of the sheath comprises a hollow member which fits tightly around the ventricular lead body so as to resist said distal movement by way of friction.

19. The implantable single-pass A-V lead, according to claim 18, wherein the resistance to distal movement is provided at least in-part by friction between an inner wall of the hollow member and an outer wall of the ventricular lead body, and wherein at least one of the inner wall and the outer wall is configured such that a resistance to movement of the distal portion of the sheath relative to the ventricular lead body is greater for distal relative movement than for proximal relative movement.

20. A method of making an implantable single-pass A-V lead that is adjustable to accommodate varying heart sizes, comprising the steps of:

forming an inner, ventricular lead body having a proximal end adapted for connection to an implantable stimulation device and a distal end for placement within the right ventricle;

attaching a ventricular electrode at the distal tip of the ventricular lead body;

forming an atrial lead body having an outer, tubular sheath with at least a first portion of the sheath slidably mounted over the ventricular lead body, the sheath further being formed with a flexible, bowing portion which forms an outwardly-extending atrial bow when the first portion of the sheath is advanced in a distal direction relative to the ventricular lead body;

forming a distal portion of the sheath to fit tightly around the ventricular lead body so as to resist sliding of the ventricular lead body therethrough by way of friction; and attaching an atrial electrode on the flexible, bowing portion of the sheath.

21. The method of making an implantable a single-pass A-V lead, according to claim 20, further comprising the step of:

forming the distal portion of the sheath such that a resistance to movement of the distal portion of the sheath relative to the ventricular lead body is greater for distal relative movement than for proximal relative movement.

22. The method of molting an implantable a single-pass A-V lead, according to claim 16, further comprising the steps of:

positioning the atrial electrode on a central region of the bowing portion; and forming the outer sheath so that the position of the atrial electrode relative to the ventricular electrode is longitudinally adjustable by sliding the first portion of the sheath toward the proximal end of the ventricular lead body, and so that the position of the atrial electrode relative to the ventricular lead body is laterally adjustable by sliding the first portion of the sheath toward the distal end relative to the ventricular lead body to increase a lateral extension of the atrial bow.

23. The method of making an implantable a single-pass A-V lead, according to claim 20, further comprising the step of:

fixedly attaching a distal portion of the sheath to the ventricular lead body.

24. The method of making an implantable single-pass A-V lead, according to claim 20, further comprising the step of:

forming the atrial electrode into a fixed, curved configuration to facilitate formation of the atrial bow when a compressive force is applied to the bowing portion; and positioning the atrial electrode in-line with the bowing portion.

25. The method of making an implantable single-pass A-V lead, according to claim 20, further comprising the step of:

forming a lumen within the sheath, the lumen being adapted for the insertion of an atrial stylet, the lumen extending into the bowing portion so that the bowing portion is held in a substantially straight configuration when the atrial stylet is inserted.

26. The method of making an implantable single-pass A-V lead, according to claim 20, further comprising the step of:

forming the bowing portion in a preformed-shape to assume a curved configuration when a tensional force is released from the bowing portion.

27. The method of making an implantable single-pass A-V lead, according to claim 20, further comprising the step of:

forming a lumen, within the ventricular lead body, that extends axially from the proximal end of the ventricular lead body substantially to the distal end of the ventricular lead body, the lumen being adapted for the insertion of a stylet.

28. A method of making an implantable single-pass A-V lead that is adjustable to accommodate varying heart sizes, comprising the steps of:

forming an inner, ventricular lead body having a proximal end adapted for connection to an implantable stimulation device and a distal end for placement within the right ventricle;

attaching a ventricular electrode at the distal tip of the ventricular lead body;

forming an atrial lead body having an outer, tubular sheath with at least a first portion of the sheath slidably mounted over the ventricular lead body, the sheath further being formed with a flexible, bowing portion which forms an outwardly-extending atrial bow when the first portion of the sheath is advanced in a distal direction relative to the ventricular lead body;

attaching an atrial electrode on the flexible, bowing portion of the sheath; and forming a lumen, within the ventricular lead body, that extends axially from the proximal end of the ventricular lead body substantially to the distal end of the ventricular lead body, the lumen being adapted for the insertion of a stylet.

29. An adjustable, single-pass implantable cardiac stimulation lead, comprising:

a first member having an atrial electrode; and a second member having a ventricular electrode, the second member slidably attached to the first member such that at least a first portion of the first member is slidable relative to the second member, at least one of the members having a locking portion that secures the members together to prevent sliding of a second portion of the first member relative to the second member while permitting the sliding of the first portion relative to the second member, whereby the sliding causes a bow to be formed in a bowing portion of the first member;

wherein the locking portion comprises a tubular portion of the first member that is configured to fit tightly around the second member.

30. An implantable single-pass A-V lead that is adjustable to accommodate varying heart sizes, comprising:

an inner, ventricular lead body having a proximal end for connection to an implantable stimulation device and a distal end for placement within the right ventricle;

a ventricular electrode at the distal tip of the ventricular lead body;

an atrial lead body having an outer, tubular sheath with at least a first portion of the sheath being slidably mounted over the ventricular lead body, the sheath having a distal end and a proximal end, and having a distal portion that is tightly coupled to the ventricular lead body such that a resistance is created to distal movement of the distal portion relative to the ventricular lead body, the sheath further having a flexible, bowing portion which forms an outwardly-extending atrial bow when the first portion of the sheath is advanced in a distal direction relative to the ventricular lead body; and an atrial electrode on the flexible, bowing portion of the sheath;

wherein a portion of the ventricular lead body along which the sheath is slidable has a length which exceeds a total length of the sheath, so that a position of the atrial electrode relative to the ventricular electrode is longitudinally adjustable by sliding the sheath proximally relative to the ventricular lead body;

and wherein the bowing portion is sufficiently elongated and flexible to allow a curvature of the atrial bow to be increased by sliding the first portion of the sheath distally along the ventricular lead body, an increase is said curvature causing an increase in a lateral displacement of the atrial electrode relative to the ventricular lead body so that the position of the atrial electrode relative to the ventricular lead body is laterally adjustable.

31. An implantable single-pass A-V lead that is adjustable to accommodate varying heart sizes, comprising:

an inner, ventricular lead body having a proximal end for connection to an implantable stimulation device and a distal end for placement within the right ventricle;

a ventricular electrode at the distal tip of the ventricular lead body;

an atrial lead body having an outer, tubular sheath with at least a first portion of the sheath being slidably mounted over the ventricular lead body, the sheath having a distal end and a proximal end, the sheath further having a flexible, bowing portion which forms an outwardly-extending atrial bow when the first portion of the sheath is advanced in a distal direction relative to the ventricular lead body; and an atrial electrode on the flexible, bowing portion of the sheath;

wherein a distal portion of the sheath comprises a hollow member which fits tightly around the ventricular lead body such that a frictional resistance is created to distal sliding of the distal portion of the sheath along the ventricular lead body.

32. An implantable single-pass A-V lead that is adjustable to accommodate varying heart sizes, comprising:

an inner, ventricular lead body having a proximal end for connection to an implantable stimulation device and a distal end for placement within the right ventricle;

a ventricular electrode at the distal tip of the ventricular lead body;

an atrial lead body having an outer, tubular sheath with at least a first portion of the sheath being slidably mounted over the ventricular lead body, the sheath having a distal end and a proximal end, the sheath further having a flexible, bowing portion which forms an outwardly-extending atrial bow when the first portion of the sheath is advanced in a distal direction relative to the ventricular lead body; and an atrial electrode on the flexible, bowing portion of the sheath;

wherein the ventricular lead body has a lumen that extends axially from the proximal end of the ventricular lead body substantially to the distal end of the ventricular lead body, the lumen adapted for the insertion of a stylet.

33. A method of making an implantable single-pass A-V lead that is adjustable to accommodate varying heart sizes, comprising the steps of:

forming an inner, ventricular lead body having a proximal end adapted for connection to an implantable stimulation device and a distal end for placement within the right ventricle;

attaching a ventricular electrode at the distal tip of the ventricular lead body;

forming an atrial lead body having an outer, tubular sheath with at least a first portion of the sheath slidably mounted over the ventricular lead body, the sheath further being formed with a flexible, bowing portion which forms an outwardly-extending atrial bow when the first portion of the sheath is advanced in a distal direction relative to the ventricular lead body;

attaching an atrial electrode on the flexible, bowing portion of the sheath; and forming a lumen within the sheath, the lumen being adapted for the insertion of an atrial stylet, the lumen extending into the bowing portion so that the bowing portion is held in a substantially straight configuration when the atrial stylet is inserted.

* * * * *